United States Patent [19]

Immer et al.

[11] 4,213,895

[45] Jul. 22, 1980

[54] N-[N-[N-[N-[N-(5-OXO-L-PROLYL)-L-HISTIDYL]-L-TRYPTOPHYL]-L-SERYL]-L-TYROSYL]GLYCINE AZIDE, AN INTERMEDIATE OF THE RELEASING AGENT OF LUTEINIZING HORMONE (LH) END OF FOLLICLE STIMULATING HORMONE (FSH)

[75] Inventors: Hans U. Immer, Mount Royal; Verner R. Nelson, Kirkland; Menfred K. Gotz, Hudson, all of Canada

[73] Assignee: American Home Products Corporation, New York, N.Y.

[21] Appl. No.: 23,563

[22] Filed: Mar. 26, 1979

Related U.S. Application Data

[60] Continuation-in-part of Ser. No. 456,343, Mar. 29, 1974, Pat. No. 4,159,980, which is a division of Ser. No. 226,508, Feb. 15, 1972, Pat. No. 3,835,108.

[51] Int. Cl.² .................. C07C 103/52; A61K 37/00
[52] U.S. Cl. .................. 260/112.5 R; 260/112.5 LH; 424/177
[58] Field of Search .............. 260/112.5 LH, 112.5 R; 424/177

[56] References Cited

PUBLICATIONS

H. Matsuo et al., Biochem. Biophys. Res. Comm., 43, 1334–1339, (1971).

*Primary Examiner*—Delbert R. Phillips
*Attorney, Agent, or Firm*—Arthur E. Wilford

[57] ABSTRACT

N-[N-[N-[N-[N-(5-Oxo-L-prolyl)-L-histidyl]-L-tryptophyl]-L-seryl]-L-tyrosyl]glycine hydrazide trifluoroacetate is converted to N-[N-[N-[N-[N-(5-oxo-L-prolyl)-L-histidyl]-L-tryptophy]-L-seryl]-tyrosyl]glycine azide, a useful intermediate for preparing LH and FSH releasing hormone.

1 Claim, No Drawings

N-[N-[N-[N-(5-OXO-L-PROLYL)-L-HISTIDYL]-L-TRYPTOPHYL]-L-SERYL]-L-TYROSYL]GLYCINE AZIDE, AN INTERMEDIATE OF THE RELEASING AGENT OF LUTEINIZING HORMONE (LW) AND OF FOLLICLE STIMULATING HORMONE (FSH)

This application is a continuation-in-part of application Ser. No. 456,343, filed Mar. 29, 1974, and now U.S. Pat. No. 4,159,980 issued July 3, 1979, which is incorporated herein by reference and in turn is a division of application Ser. No. 226,508, filed Feb. 15, 1972 and now U.S. Pat. No. 3,835,108, issued Sept. 10, 1974.

BACKGROUND OF THE INVENTION

1. Field of the Invention

This invention relates to a process for preparing the releasing hormone of luteinizing hormone (LH) and of follicle stimulating hormone (FSH) in the form of an acid addition salt, to salts thereof with pharmaceutically acceptable acids, to pharmaceutical compositions containing said LH and FSH-releasing hormone, and to intermediates obtained in said process.

LH and FSH are both gonadotrophic hormones elaborated by the pituitary gland of humans and of animals. LH together with FSH stimulates the release of estrogens from the maturing follicles in the ovary and induces the process of ovulation in the female. In the male, LH stimulates the interstitial cells and is for that reason also called interstitial cell stimulating hormone (ICSH). The follicle-stimulating hormone (FSH) induces maturation of the follicles in the ovary and together with LH, plays an important role in the cyclic phenomena in the female. FSH promotes the development of germinal cells in the testes of the male. Both LH and FSH are released from the pituitary gland by the action of LH- and FSH-releasing hormones, and there is good evidence that said releasing hormone is elaborated in the hypothalamus and reaches the pituitary gland by a neurohumoral pathway, see e.g. Schally et al., Recent Progress in Hormone Reserach 24, 497 (1968).

The LH- and FSH-releasing hormone has been isolated from pig hypothalami and its constitution elucidated by Schally et al., Biochem. Res. Commun. 43, 393 and 1334 (1971), who proposed the decapeptide structure (pyro) glu-His-Trp-Ser-Tyr-Gly-Leu-Arg-Pro-Gly-NH₂.

This constitution has been confirmed by syntheses (see below), and the LH- and FSH-releasing hormone may also be represented in a somewhat more modern terminology by the formula 1

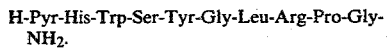

(1.)

2. Description of Prior Art

The LH- and FSH-releasing hormone has been synthesized by Sievertsson et al., Biochem Biophys. Res. Commun. 44, 1566 (1971) by a combination of classical and solid-phase (Merrifield) methods; the same hormone has also been synthesized by Geiger et al., ibid. 45, 767 (1971) using a strictly classical method; by Matsuo et al., ibid. 45, 822 (1971) using a solid-phase method; and by Monahan et al., C. R. Acad. Sci., Ser. D, 273, No. 4,508 (1971) using a solid-phase method. In contradistinction to the processes of the references cited above the process of this invention is simpler and more efficient in giving considerably better over-all yields than any of the known procedures. It is a particular advantage of the process of this invention that it requires only a minimum of protective groups for the intermediates, especially where secondary functions are concerned. Thus, the hydroxyl group in serine does not have to be protected; the NH-groups in tryptophan and in histidine do not require protection; and no protection for the guanidino function in arginine and for the hydroxyl group of tyrosine is necessary in the later stages of the process. The process of this invention is thus also more convenient and less cumbersome than the processes of Prior Art. An added advantage of the process of this invention is the fact that the final step thereof consists in the condensation of two unprotected fragments, each of which is well defined, easy to purify, and each obtainable in a high state of purity. The final product thus obtained is the free, unprotected decapeptide which does not require any deprotective steps and is obtained in a high degree of purity and in good yields.

In the following text, the term "lower alkyl" designates a straight or branched chain alkyl group containing from 1–5 carbon atoms and includes methyl, ethyl, propyl, isopropyl, n-butyl, sec-butyl, t-butyl and the like. The term "lower" indicates 1–6 carbon atoms. The term "strong organic base" denotes aliphatic and heterocyclic tertiary nitrogen bases and includes triethylamine, dibutylmethylamine, N-methylpyrrolidine, N-methylpiperidine, N-methylpiperazine, N-methylmorpholine and the like; triethylamine is preferred. The term "halogenated hydrocarbon" denotes those having from 1–2 carbon atoms and includes methylene dichloride, ethylene dichloride, chloroform and the like; chloroform is preferred. The term "strong mineral acid" when used in conjunction with an anhydrous system, denotes hydrogen chloride, hydrogen bromide, and sulfuric acid; hydrogen chloride is preferred; when used in conjunction with an aqueous system the term includes any common mineral acid.

L-Pyroglutamic acid is the lactam of L-glutamic acid and has the structure of 5-oxo-L-proline.

Many of the methods used in the syntheses of peptide linkages are commonly designated by trivial names. Thus, the "azide method" comprises the reaction of an amino acid hydrazide having a suitably protected amino group with a nitrite, usually t-butyl or isoamyl nitrite, to obtain the corresponding azide which is then reacted with an amino acid having a free amino and a suitably protected carboxylic acid group, to obtain the desired peptide.

The condensation with dicyclohexylcarbodiimide comprises the reaction of an amino acid having a suitably protected amino and a free carboxylic acid group with another amino acid having a free amino and a suitably protected carboxylic acid group; the peptide linkage is formed with elimination of the elements of water and formation of dicyclohexylurea which is easily removed from the reaction mixture. In the case where the free amino group of the second amino acid reacts only with difficulty, for example if the free amino group is secondary such as in proline, it is advantageous to add hydroxysuccinimide to the reaction to form the intermediate hydroxysuccinimide ester of the first amino acid which reacts readily with a secondary amino group to form the desired peptide linkage. In principle, this modification of the dicyclohexylcarbodiimide method involves an activation of the carboxylic acid group, and such activation is also obtained when the 4-nitrophenyl or 2,4-dinitrophenyl or 2,4,5-trichlorophenyl esters of the carboxylic acid are used instead of the free acid. Such esters are generally known as activated esters.

The protective groups used in the process of this invention, and the conventional abbreviations by which they and the common amino acids are designed, are described in Schröder and Lübke, The Peptides, Academic Press, New York and London 1965.

SUMMARY OF THE INVENTION

The process of this invention is summarily described in the following steps:

N-(-b 5-Oxo-L-prolyl)-L-histidine hydrazide, obtained as described by Gillessen et al., Helv. Chim. Acta 53, 63 (1970), is condensed by means of the azide method with a lower alkyl or aralkyl ester of L-tryptophan, preferably the benzyl ester obtained as described by Wilchek et al., J. Org. Chem. 28, 1874 (1963), to yield N-[N-(5-oxo-L-prolyl)-L-histidyl]-L-tryptophan benzyl ester: The latter is treated with hydrazine hydrate to yield N-[N-(5-oxo-L-prolyl)-L-histidyl]-L-tryptophan hydrazide (II).

A lower alkyl ester of N-[O-benzyl-N-carboxy-L-tyrosyl]glycine N-benzyl ester, preferably the methyl ester prepared as described by Morley, J. Chem Soc. (C), 2410,(1967) is hydrolyzed to the corresponding free acid which is converted to the corresponding mixed anhydride with ethyl chloroformate and treated with t-butyl carbazate to yield N-[O-benzyl-N-carboxy-L-tyrosyl]glycine N-benzyl ester 2-carboxyhydrazide t-butyl ester, and said last-named compound is hydrogenolyzed by means of hydrogen and a noble metal catalyst to yield N-L-tyrosylglycine 2-carboxyhydrazide t-butyl ester. Condensation of said last-named compound with an activated ester of N-carboxy-L-seryl N-benzyl ester, preferably the 2,4-dinitrophenyl ester prepared as described by Marchiori et al., Gazz. Chim. Ital. 93, 834 (1963) yields N-[N-(N-carboxy-L-seryl)-L-tyrosyl]glycine N-benzyl ester 2-carboxyhydrazide t-butyl ester which is hydrogenolyzed as above to yield N-(N-L-seryl-L-tyrosyl)glycine 2-carboxyhydrazide t-butyl ester (III).

N-carboxy-L-proline N-benzyl ester, prepared as described by Berger et al., J. Am. Chem. Soc., 76, 5552 (1954) is condensed with a glycine lower alkyl ester, preferably the ethyl ester, using dicyclohexylcarbodiimide as the condensing agent and the resulting product is treated with ammonia to obtain 2-[(N-carboxy-L-prolyl)amino]-acetamide N-benzyl ester. Said last-named compound is hydrogenolyzed and condensed with N-carboxy-N$^G$-nitro-L-arginine N-t-butyl ester, obtained as described by Hofmann et al., J. Am. Chem. Soc., 87, 620 (1965), using N-hydroxysuccinimide and dicyclohexylcarbodiimide as the condensing agents, to obtain N-[N-(N-carboxy-N$^G$-nitro-L-arginyl)-L-prolyl]glycinamide N-t-butyl ester (IV).

The same compounds IV is also prepared by the following alternative route.

A lower alkyl ester of L-proline, preferably the methyl ester, and N-carboxy-N$^G$-nitro-arginine N-t-butyl ester, prepared respectively as described by Boissonas et al., Helv. Chim. Acta 44, 123 (1961) and by Hofmann et al. cited above, are condensed by means of dicyclohexylcarbodiimide to yield N-(N-carboxy-N$^G$-nitro-L-arginyl)-L-proline N-t-butyl ester. Said last-named compound is condensed with a glycine lower alkyl ester, preferably the ethyl ester, using dicyclohexylcarbodiimide as the condensing agent and the resulting product is treated with ammonia to obtain N-[N-(N-carboxy-N$^G$-nitro-L-arginyl)-L-prolyl]-glycinamide N-t-butyl ester (IV), identical with the product obtained as described above. The protective t-butoxycarbonyl group of said last-named compound is removed by treatment with acid and the resulting product is condensed with an activated ester of N-carboxy-L-leucine N-benzyl ester, preferably the 2,4,5-trichlorophenyl ester prepared as described by Kenner et al., J. Chem. Soc., 761 (1968), to yield N-[N-[N-(N-carboxy-L-leucyl)-N$^G$-nitro-L-arginyl]-L-prolyl]glycinamide N-benzyl ester which is hydrogenolyzed in glacial acetic acid by means of hydrogen and a noble metal catalyst to remove the protective nitro and carbobenzoxy groups to yield the corresponding diacetate salt, N-[N-[N-(N-L-leucyl)-L-arginyl]-L-prolyl]-glycinamide diacetate (V).

N-[N-(5-Oxo-L-prolyl)-L-histidyl]-L-tryptophan hydrazide (II) and N-(N-L-seryl-L-tyrosyl)glycine 2-carboxyhydrazide t-butyl ester (III), both obtained as described above, are condensed by means of the azide method to yield the hexapeptide N-[N-[N-[N-(5-oxo-L-prolyl)-L-histidyl]-L-tryptophyl]-L-seryl]-L-tyrosyl]glycine 2-carboxyhydrazide t-butyl ester. The same compound is also obtained by condensation of N-[N-(5-oxo-L-prolyl)-L-histidyl]-L-tryptophan, obtained from the corresponding benzyl ester described above by hydrogenolysis, with N-(N-L-seryl-L-tyrosyl)glycine 2-carboxyhydrazide t-butyl ester (III), obtained as described above, using dicyclohexylcarbodiimide as the condensing agent. N-[N-[N-[(5-oxo-L-prolyl)-L-histidyl]-L-tryptophyl]-L-seryl]-L-tyrosyl]glycine 2-carboxyhydrazide t-butyl ester obtained by either of the above routes is treated with trifluoroacetic acid to yield the trifluoroacetic acid salt of the hexapeptide hydrazide, viz. N-[N-[N-[N-(5-oxo-L-prolyl)-L-histidyl]-L-tryptophyl]-L-seryl]-L-tyrosyl]glycine hydrazide trifluoroacetate (VI).

Said last-named compound (VI) is condensed by means of the azide method via the azide, N-[N-[N-[N-(5-oxo-L-prolyl)-L-histidyl]-L-tryptophyl]-L-seryl]-L-tyrosyl]glycine azide, with N-[N-[N-(N-leucyl)-L-arginyl]-L-prolyl]glycinamide diacetate (V) to yield the desired decapeptide 5-oxo-L-prolyl-L-histidyl-L-tryptophyl-L-seryl-L-tyrosylglycyl-L-leucyl-L-arginyl-L-prolylglycinamide (I) which is isolated in the form of its diacetate salt. The latter salt may be converted, if desired, into a different acid addition salt, e.g. a salt with a pharmaceutically acceptable acid, by treatment with the appropriate ion exchange resin in the manner described by Boissonas et al., Helv. Chim. Acta 43, 1349 (1960). Suitable ion exchange resins are strongly basic anion exchange resins, for example those listed in Greenstein and Winitz "Chemistry of the Amino Acids", Hohn Wiley and Sons, Inc., New York and London 1961, Vol. 2, p. 1456. Basically substituted cross-linked polystyrene resins such as Amerlite IRA-400 or IRA-410 are preferred. The above diacetate may also be converted to a salt of low solubility in body fluids by treatment with a slightly water-soluble pharmaceutically acceptable acid. The acid addition salts of the LH- and FSH-releasing hormone produced by the process of this invention with pharmacologically acceptable acids are biologically fully equivalent to the natural hormone.

DETAILED DESCRIPTION OF THE INVENTION

1. LH- and FSH-Releasing Activity

The synthetic product of formula I obtained by the process of this invention in the form of an acid addition salt possesses LH- and FSH-releasing properties and is as active as the natural hormone when tested in the radioimmunoassay described by Niswender et al. Proc. Soc. Exp. Biol. Med., 128, 807 (1968). It is equally active in the assay determining induction of ovulation in the hamster described by Arimura et al., Science 174, 511 (1971), and in a modification of the similar assay in the rat described by Arimura et al. in Endrocinology 80, 515 (1967).

2. Preparation of Compounds

The process of this invention is carried out in the following manner.

N-[N-[N-[N-(5-oxo-L-prolyl)-L-histidyl]-L-tryptophyl]-L-seryl]-L-tyrosyl]glycine hydrazide trifluoroacetate (VI) is dissolved in an inert anhydrous solvent, preferably a mixture of dimethylformamide and dimethylsulfoxide, and a solution of a strong mineral acid, preferably hydrogen chloride, in an anhydrous ether or cyclic ether, preferably tetrahydrofuran, is added with stirring at a temperature of from −10° C. to 5° C., preferably at about 0° C. The mixture is cooled to a temperature of from about −30° C. to about −10° C., preferably to about −20° C., a solution of a substantially equimolar amount of an organic nitrite, preferably t-butyl nitrite or isoamyl nitrite, in dimethylformamide is added and the mixture is stirred at about −30° C. to about −10° C. for 30–60 minutes. A sufficient amount of a strong organic base, preferably triethylamine, is added to make the mixture slightly alkaline, preferably pH 8–9 giving a solution of N-[N-[N-[N-(5-oxo-L-prolyl)-L-histidyl]-L-tryptophyl]-L-seryl]-L-tyrosyl]glycine azide. A solution of a substantially equimolar amount of N-[N-[N-(N-L-leucyl)-L-arginyl]-L-propyl]-glycinamide diacetate (V, obtained as described in aforementioned U.S. Pat. No. 4,159,980 above) in an anhydrous inert solvent, preferably dimethylformamide, is added together with a quantity of a strong organic base, preferably triethylamine, sufficient to neutralize the diacetate salt. The mixture is stirred at a temperature of from about −30° C. to about −10° C. for 30–60 minutes, then at about 0° C. for another 30–60 minutes, and finally with cooling in an ice bath for 16–24 hours. Filtration, evaporation of the filtrate, taking up the residue in a lower alkanol, preferably methanol, and precipitation by addition on an ether, preferably diethyl ether, yields the crude decapeptide which is purified by partition chromatography on a chemically modified cross-linked dextran ("Sephadex LH-20") using the lower phase of a n-butanol-acetic acid-water mixture as solvent. Evaporation of the eluates, taking up the residue in a lower alkanol, preferably methanol, and precipitation by addition of an ether, preferably diethyl ether, yields the substantially pure decapeptide 5-oxo-L-prolyl-L-histidyl-L-tryptophyl-L-seryl-L-tyrosylglycyl-L-leucyl-L-arginyl-L-prolylglycinamide (I), isolated as the diacetate salt which shows the same amino acid analysis as the natural product and which is as potent as the latter in bioassays. If desired, the above diacetate salt may be converted into other acid addition salts, preferably those with pharmaceutically acceptable acids.

The following Examples will illustrate the invention. All compounds are identified by elementary analysis.

EXAMPLE 1

5-Oxo-L-Prolyl-L-Histidyl-L-Tryptophyl-L-Seryl-L-Tyrosylglycyl-L-Leucyl-L-Arginyl-L-Prolylglycinamide (I) Diacetate via N-[N-[N-[N-(5-Oxo-L-Prolyl)-L-Histidyl]-L-Tryptophyl]-L-Seryl]-L-Tyrosyl]Glycine Azide N-[N-[N-[N-(5-Oxo-L-prolyl)-L-histidyl]-L-tryptophyl]-L-seryl]-L-tyrosyl]glycine hydrazide trifluoroacetate (VI, Ex. 17 of the aforementioned parent application, Ser. No. 456,343, now U.S. Pat. No. 4,159,980, 0.840 g, 0.762 mmol) is dissolved at 0° C. in a mixture of dry dimethylformamide (3.7 ml), dry dimethylsulfoxide (3.3 ml) and 1.65 N anhydrous gaseous hydrogen chloride in dry tetrahydrofuran (2.77 ml). The solution is cooled to −20° C. and a 10% solution of isoamyl nitrite in dry dimethylformamide (1.12 ml, 0.83 mmol) is added with stirring. The solution is stirred for 30 minutes at −20° C. and then cooled to −25° C. Triethylamine (0.7 ml) is slowly added until the solution is slightly alkaline, pH 8–9, providing an organic solution of N-[N-[N-[N-(5-oxo-L-prolyl)-L-histidyl]-L-tryptophyl]-L-seryl]-L-tyrosyl]glycine azide. While stirring at −20° C., a solution of N-[N-[N-(N-L-leucyl)-L-arginyl]-L-prolyl]-glycinamide diacetate (V, Example 15 of the aforementioned parent application, Ser. No. 456,343, now U.S. Pat. No. 4,159,980, 0.427 g, 0.762 mmol) in dry dimethylformamide (4.5 ml) and triethylamine (0.28 ml) is added. The resulting solution is stirred at −20° C. for 30 minutes, at 0° C. for 30 minutes and at ice bath temperature for 18 hours. The solution is filtered and the precipitate is washed with dry dimethylformamide (2×2 ml). The combined filtrates are concentrated under reduced pressure at 40° C. The residue is dissolved in methanol (5 ml), and diethyl ether (500 ml) is slowly added. The precipitate is collected, dried and purified by partition chromatography on a chemically modified cross-linked dextran ("Sephadex LH-20") using the lower phase of n-butanol-acetic acid-water (8:4:40). The combined fractions are concentrated to dryness under reduced pressure at 45° C., dissolved in methanol (5 ml) and added to diethyl ether (250 ml). The precipitate is collected by filtration and dried to yield the title compound with $[\alpha]_D^{25}$ −53.50° (c=1.0, 1% aqueous acetic acid), isolated as the diacetate salt. Amino acid analysis gives the following composition:

| Histidine | 1.0 | 1.04 | Proline | 0.96 | 1.03 |
|---|---|---|---|---|---|
| Arginine | 0.95 | 0.93 | Glycine | 2.01 | 1.98 |
| Serine | 0.90 | 0.86 | Leucine | 0.86 | 1.02 |
| Glutamic Acid | 1.07 | 1.04 | Tyrosine | 1.12 | 1.04 |

Electrophoresis at pH 1.6 in 8% aqueous formic acid and at 3500 volt gives a single spot and shows the uniformity of the compound.

In the same manner, when using t-butyl nitrite instead of isoamyl nitrite, the title compound is also obtained.

If desired, the above diacetate salt is treated with Amberlite IRA-400 or IRA-410, previously converted to a salt thereof with a pharmaceutically acceptable acid. Elution yields the corresponding salt of the title compound. Alternatively, the above diacetate salt is treated in aqueous solution with an alkali metal salt of tannic, alginic, or pamoic acid and the corresponding tannate, alginate or pamoate salt of the hormone is isolated by filtration or centrifugation.

We claim:
1. N-[N-[N[N-[N-(5-Oxo-L-prolyl)-L-histidyl]-L-tryptophyl]-L-seryl]-L-tyrosyl]glycine azide.

* * * * *